(12) United States Patent
Haverkost et al.

(10) Patent No.: US 10,349,947 B2
(45) Date of Patent: Jul. 16, 2019

(54) VASCULAR OCCLUSION DEVICES

(71) Applicant: Boston Scientific Scimed, Inc., Maple Grove, MN (US)

(72) Inventors: Patrick A. Haverkost, Brooklyn Center, MN (US); Joseph Michael Connolly, Minneapolis, MN (US); Joel N. Groff, Delano, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

(21) Appl. No.: 15/047,217

(22) Filed: Feb. 18, 2016

(65) Prior Publication Data
US 2016/0235413 A1   Aug. 18, 2016

Related U.S. Application Data

(60) Provisional application No. 62/117,503, filed on Feb. 18, 2015.

(51) Int. Cl.
*A61B 17/12*  (2006.01)

(52) U.S. Cl.
CPC .. *A61B 17/12109* (2013.01); *A61B 17/12031* (2013.01); *A61B 17/12145* (2013.01); *A61B 17/12163* (2013.01); *A61B 17/12172* (2013.01); *A61B 2017/1205* (2013.01); *A61B 2017/12054* (2013.01)

(58) Field of Classification Search
CPC ........ A61B 17/12031; A61B 17/12109; A61B 17/12145; A61B 17/12163; A61B 17/12172; A61F 2/01; A61F 2002/001; A61F 2002/016; A61F 2002/018

USPC ........................................................ 606/200
See application file for complete search history.

(56) References Cited

U.S. PATENT DOCUMENTS

| 6,080,182 | A |  | 6/2000 | Shaw et al. |
| 6,152,144 | A |  | 11/2000 | Lesh et al. |
| 6,485,524 | B2 | * | 11/2002 | Strecker ........... A61B 17/12022 623/1.15 |
| 6,530,939 | B1 |  | 3/2003 | Hopkins et al. |
| 7,252,675 | B2 |  | 8/2007 | Denison et al. |
| 8,182,508 | B2 |  | 5/2012 | Magnuson et al. |
| 10,111,676 | B2 | * | 10/2018 | Tekulve ............... A61B 17/221 |
| 2006/0241675 | A1 | * | 10/2006 | Johnson .................... A61F 2/01 606/200 |

(Continued)

FOREIGN PATENT DOCUMENTS

| JP | 2000300571 | 10/2000 |
| JP | 2014205053 | 10/2014 |

OTHER PUBLICATIONS

O. Pellerin et al., "Microvascular plug: a new embolic material for hepatic arterial skeletonization," Cardiovasc Intervent Radiol. Dec. 2014;37(6):1597-601. doi: 10.1007/s00270-014-0889-y. Epub Apr. 11, 2014.

*Primary Examiner* — Martin T Ton

(57) ABSTRACT

The present disclosure provides occlusion devices which comprise (a) a self-expanding support frame having a longitudinal axis comprising a plurality of loops each having an orifice, the support frame being self-expandable from a constrained shape to an unconstrained shape, and (b) a covering material covering an orifice of at least one of the loops. Also provided are assemblies and kits that contain such occlusion devices, and methods of delivering such occlusion devices to a patient.

20 Claims, 5 Drawing Sheets

(56) References Cited

U.S. PATENT DOCUMENTS

| | | |
|---|---|---|
| 2007/0067021 A1 | 3/2007 | Haverkost et al. |
| 2011/0054515 A1 | 3/2011 | Bridgeman et al. |
| 2012/0245614 A1 | 9/2012 | Drasler |
| 2013/0138138 A1 | 5/2013 | Clark et al. |
| 2014/0135817 A1 | 5/2014 | Tischler et al. |
| 2014/0330303 A1* | 11/2014 | Hansen ............ A61B 17/12109 606/200 |

* cited by examiner

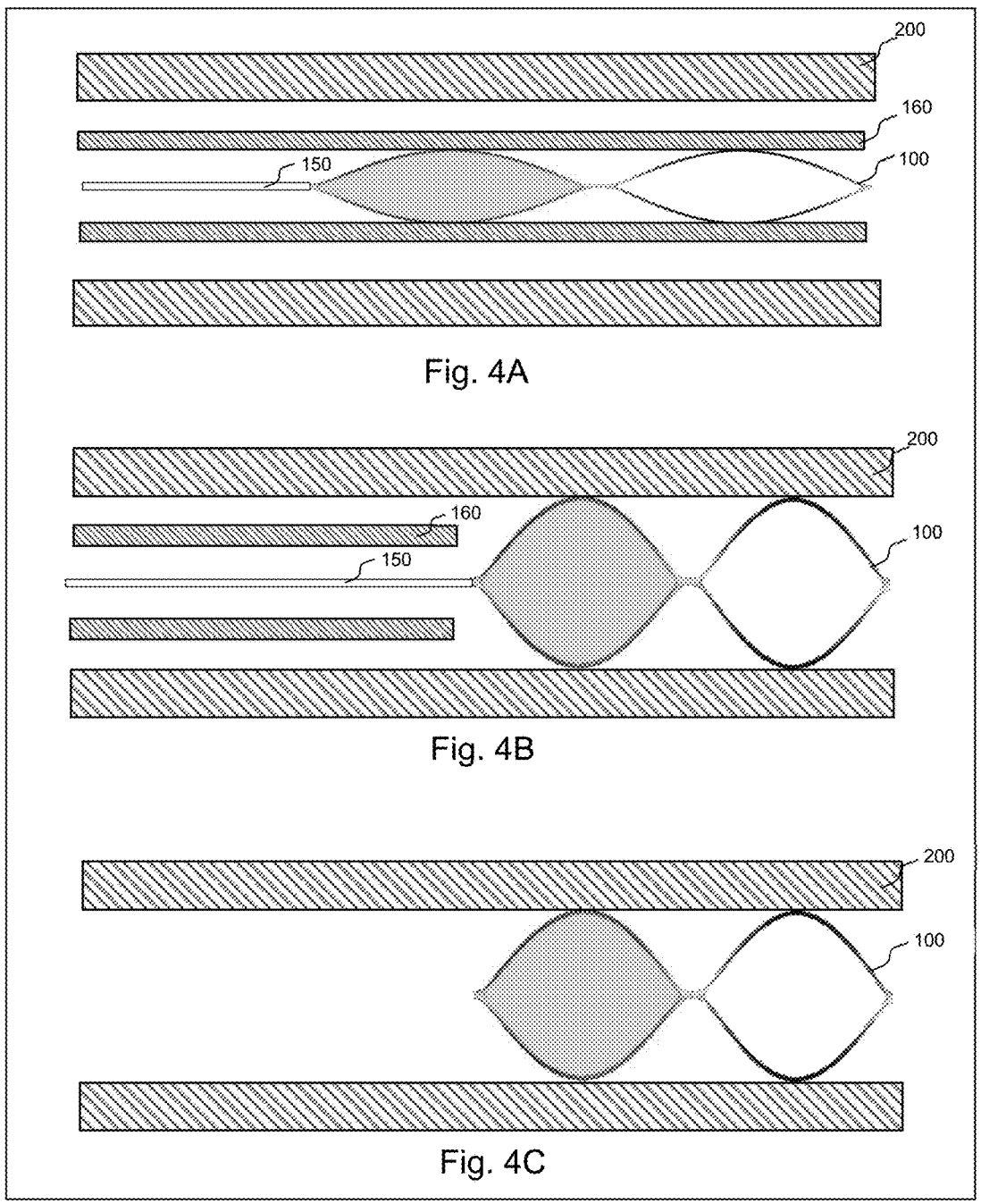

VASCULAR OCCLUSION DEVICES

CROSS-REFERENCE TO RELATED APPLICATIONS

This application claims the benefit of U.S. Provisional Application No. 62/117,503, entitled "Vascular Occlusion Devices" and filed Feb. 18, 2015, which is hereby incorporated by reference in its entirety.

FIELD

This application relates generally to devices, assemblies and kits for creating vascular occlusions and to methods for creating vascular occlusions using the same.

BACKGROUND

The endovascular treatment of a variety of conditions throughout the body is an increasingly important form of therapy. Blood vessel occlusion devices are known which are placed within the vasculature of the body in order to form a physical barrier to blood flow and/or promote thrombus formation at the site.

The present disclosure pertains to improved devices, assemblies, kits and methods for occlusion of body lumens including blood vessels, among others.

SUMMARY

In various aspects, occlusion devices are provided which comprise the following: (a) a self-expanding support frame having a longitudinal axis comprising a plurality of loops each having an orifice, the support frame being self-expandable from a constrained shape to an unconstrained shape, and (b) a covering material covering an orifice of at least one of the loops.

In some embodiments, the occlusion devices may comprise from two to eight loops (i.e., two, three, four, five, six, seven or eight loops).

In some embodiments, which may be used in combination with any of the above aspects and embodiments, at least one loop may be uncovered.

In some embodiments, which may be used in combination with any of the above aspects and embodiments, the loops may have a substantially circular shape when the support frame is viewed axially.

In some embodiments, which may be used in combination with any of the above aspects and embodiments, the support frame may comprise a series of elliptical loops.

In some embodiments, which may be used in combination with any of the above aspects and embodiments, the occlusion device is in the unconstrained shape, each loop may range from 60° to 170° out of coplanar with an adjacent loop.

In some embodiments, which may be used in combination with any of the above aspects and embodiments, an elevation view of the support frame may comprise a cosinusoidal shape. The cosinusoidal shape may comprise inflection points having tangents that range from 30° to 85° relative to the longitudinal axis when in the unconstrained shape, among other values.

In some embodiments, which may be used in combination with any of the above aspects and embodiments, the occlusion device may further comprise an attachment feature.

In some embodiments, which may be used in combination with any of the above aspects and embodiments, the occlusion device may further comprise a plurality of anchors.

In some embodiments, which may be used in combination with any of the above aspects and embodiments, the support frame may comprise nitinol.

In some embodiments, which may be used in combination with any of the above aspects and embodiments, the covering material may comprise a porous woven or non-woven polymeric sheet.

In some embodiments, which may be used in combination with any of the above aspects and embodiments, the occlusion device may be compressed and preloaded into a tubular device (e.g., catheter, sheath, etc.) in a constrained shape.

In other aspects, the present disclosure provides assemblies that comprise (a) an occlusion device in accordance with any of the above aspects and embodiments and (b) an elongated delivery member that is configured to be attached to and detached from the occlusion device.

In other aspects, the present disclosure provides kits that comprise an occlusion device or assembly in accordance with any of the above aspects and embodiments.

In still other aspects, the present disclosure provides methods of treatment that comprise (a) introducing an occlusion device in accordance with any of the above aspects and embodiments into a blood vessel while in a constrained shape and (b) removing a constraint that maintains the occlusion device in the constrained shape such that the support frame self-expands, the loops contact a wall of the blood vessel, and the covering material impedes flow through the blood vessel.

In some embodiments, the constraint may be removed by ejecting the occlusion device from a tubular medical device.

In some embodiments, which may be used in combination with any of the above aspects and embodiments, the blood vessel may be selected from a gastroduodenal artery, a hypogastric artery, and right gastric artery.

The body lumen occlusion devices described herein are advantageous for use in a variety of procedures in that they are configured to form an embolus with only a single deployment. The body lumen occlusion devices described herein are also advantageous in that they resist kickback into a parent artery (e.g., when placed at a body lumen ostium).

These and other aspects, embodiments and advantages of the present disclosure will become immediately apparent to those of ordinary skill in the art upon review of the detailed description and claims to follow.

BRIEF DESCRIPTION OF THE DRAWINGS

FIGS. 4A-4C are schematic partial cross-sectional views showing the deployment in a body lumen (e.g., blood vessel) of an occlusion device in accordance with an embodiment of the present disclosure;

Unless otherwise provided in the following specification, the drawings are not necessarily to scale, with emphasis being placed on illustration of the principles of the disclosure.

DETAILED DESCRIPTION

A more complete understanding of the present disclosure is available by reference to the following detailed description of numerous aspects and embodiments of the disclosure. The detailed description which follows is intended to illustrate but not limit the disclosure.

The terms "proximal" and "distal" generally refer to the relative position, orientation, or direction of an element or action, from the perspective of a clinician using the medical device, relative to one another. Thus, "proximal" may generally be considered closer to the clinician or an exterior of a patient, and "distal" may generally be considered to be farther away from the clinician, along the length or beyond the end of the medical device.

The present disclosure pertains to devices, assemblies and kits for creating body lumen occlusions, including blood vessel occlusions. The occlusion devices of the present disclosure are collapsible to fit within a tubular device such as a catheter or delivery sheath and, when removed from the tubular device, can naturally expand toward an unconstrained configuration to fully occlude a body lumen such as a blood vessel. For example, in certain embodiments pertaining to blood vessels, the occlusion devices may be pushed through and/or from the distal end of a catheter (e.g., ranging from 0.021" inner diameter (ID) microcatheter to a 0.070" ID guide sheath, among other possibilities) that is in place at the site of embolization. Upon exiting the catheter, the device will automatically expand to engage a wall of the blood vessel, occluding the same.

Figure 1A:
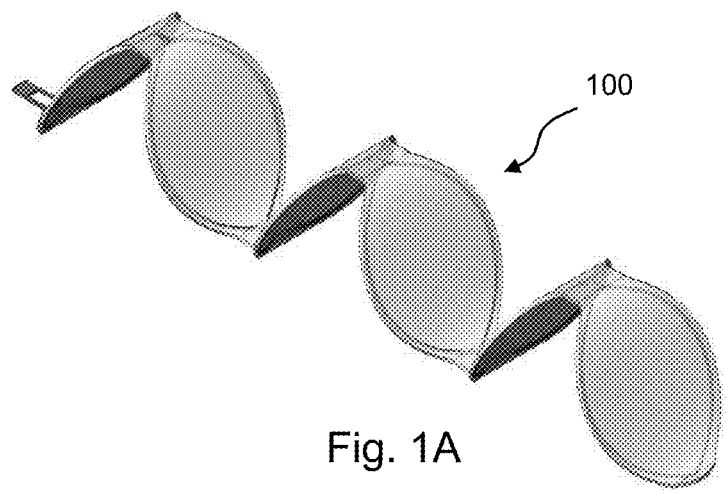
FIG. 1A is a schematic perspective view of a self-expanding occlusion device in accordance with an embodiment of the present disclosure.
Figure 1B:
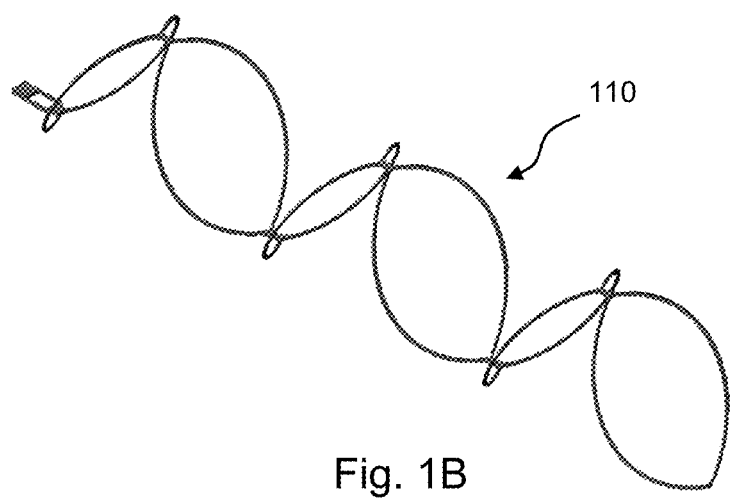
FIG. 1B is a schematic perspective view of a support frame of the occlusion device of FIG. 1A.
Figure 1C:
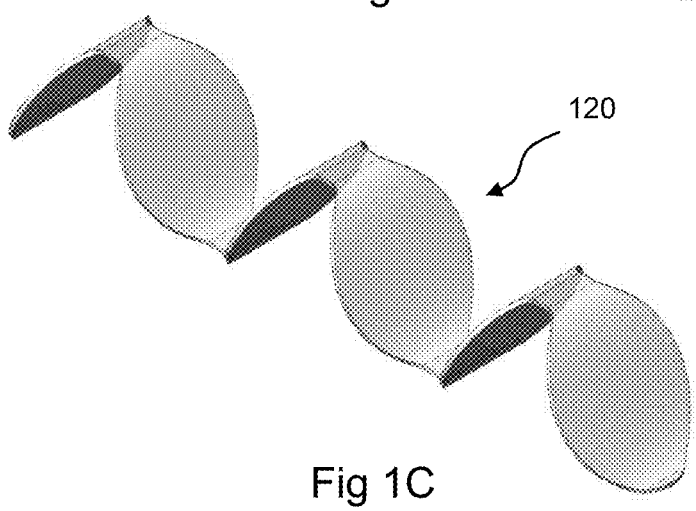
FIG. 1C is a schematic perspective view of a covering material of the occlusion device of FIG. 1A.

FIG. 1A is a schematic perspective view of a self-expanding occlusion device 100 in an unconstrained state, in accordance with an embodiment of the present disclosure. FIGS. 1B and 1C are schematic perspective views of a support frame 110 and a covering material 120 of the occlusion device 100 of FIG. 1A.

Figure 2A:
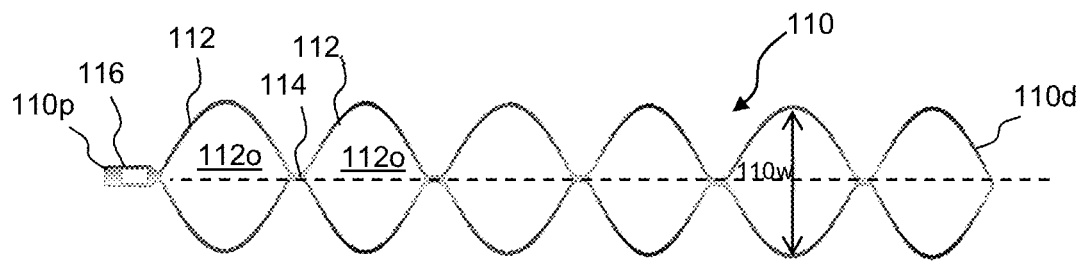
FIGS. 2A-2D are views of a support frame of the occlusion device of FIG. 1A, taken from four different perspectives.
Figure 2B:
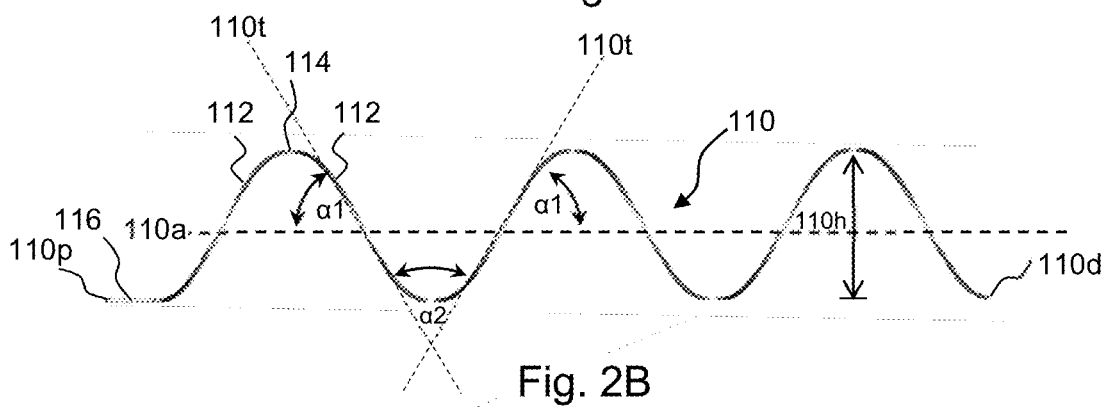

Turning first to the support frame 110, FIGS. 2A and 2B are schematic plan and elevation views, respectively, of the support frame 110 of the occlusion device 100 of FIG. 1A. As seen from these FIGS, the occlusion device 100 generally comprise a support frame 110 having a proximal end 110p, a distal end 110d, an axis 110a, a width 110w and a height 110h. As will become apparent from the discussion below, the width 110w and the height 110h are the same in the illustrated embodiment, because the device has a circular axial profile. The support frame of the present disclosure comprises at least two loops 112 (six shown) each having an orifice 112o (two numbered), The loops 112 are connected to one another Via connection regions 114. As can be seen from the plan view of FIG. 2A, the loops 112 are substantially elliptical in shape, with adjacent pair of loops forming a "figure eight" when viewed from this perspective. From the elevation view of FIG. 2B, on the other hand, the frame has a sinusoidal shape (specifically, a cosinusoidal shape). Tangent lines 110t drawn through the inflection points of the loops have an angle α1 relative to the longitudinal axis 110a. When in the unconstrained expanded shape, the angle α1 may take on a variety of values. In certain embodiments, the angle α1 may range, for example, from 30° or less to 85° or more, for example, ranging from 30° to 35° to 40° to 45° to 50° to 55° to 60° to 65° to 70° to 75° to 80° to 35° (i.e., ranging between any two or the preceding numerical values), among other possible values. Adjacent tangent lines 110t in turn intersect at an angle α2. The relationship between angle α1 and angle α2 is α1=(180°−α2)/2 or α2=180°−2α1. As will be appreciated by those skilled in the art, the more eccentric the substantially elliptical in shape (e.g., as viewed from the perspective of FIG. 2A), the smaller the value of angle α1, whereas the less eccentric the substantially elliptical in shape viewed from the perspective of FIG. 2A, the greater the value of the angle α1. Angle α2 provides a measure of the degree to which adjunct loops deviate from being substantially coplanar with one another when in an unconstrained shape, wherein a value for angle α2 of 180° means that the adjacent loops are coplanar and wherein in certain beneficial embodiments, each loop may range from 60° to 170° out of coplanar with an adjacent loop, meaning that the value of angle α2 may range from 10° to 120°. In some embodiments, each loop may range from 80° to 150° out of coplanar with an adjacent loop, meaning that the value of angle α2 may range from 30° to 100°.

The thin elements that form the loops 112 may be of substantially any cross-sectional geometry and are commonly of substantially rectangular geometry (ignoring a small amount of curvature, for example, where the support frame is cut from a tube a discussed below). Typical maximum thicknesses for the thin elements that form the loops 112 may range, for example, from 0.002" to 0.010" (0.05 mm to 0.25 mm), more typically about 0.004" (0.1 mm), among other values, and will typically vary with the size of the device.

The support frame 110 shown further includes an attachment feature 116 for attachment to and detachment from an elongate delivery member as discussed below. While the attachment feature 116 shown is of a unitary structure with the support frame 110, attachment feature 116 may also be provided in the form of a separate component that is attached to the support frame, for example, soldered, welded, fused, glued, crimped, or otherwise joined together to form the frame.

Figure 2C:
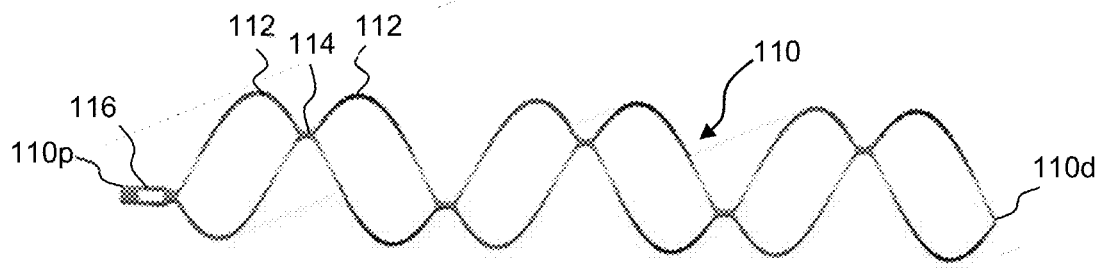
Figure 2D:
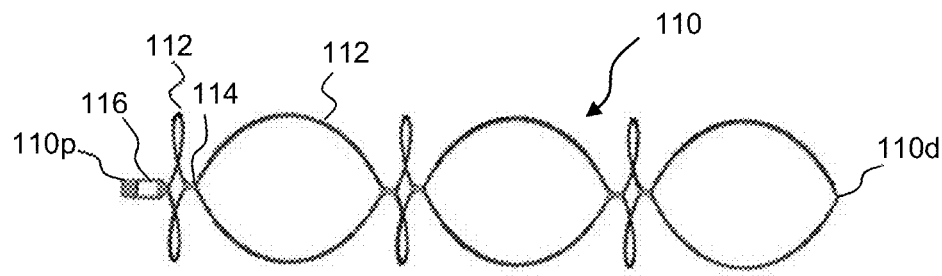

FIGS. 2C and 2D show the support frame 110 of the occlusion device of FIG. 1A from two additional views. As can be seen from the perspective of FIG. 2O, the loops 112 are substantially planar in shape, with curvature occurring predominantly in the loop connection regions 114, which act as joints for the loops 112.

Figure 3A:
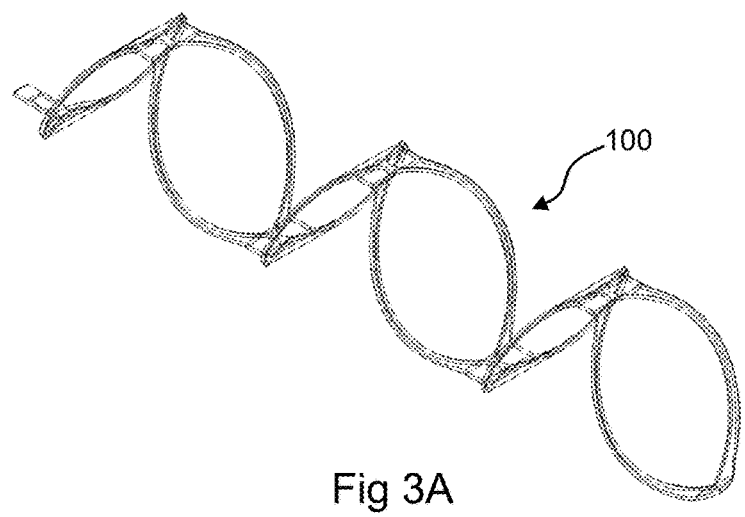
FIGS. 3A-3D are wireframe illustrations of the occlusion device of FIG. 1A, taken from different perspectives.
Figure 3B:
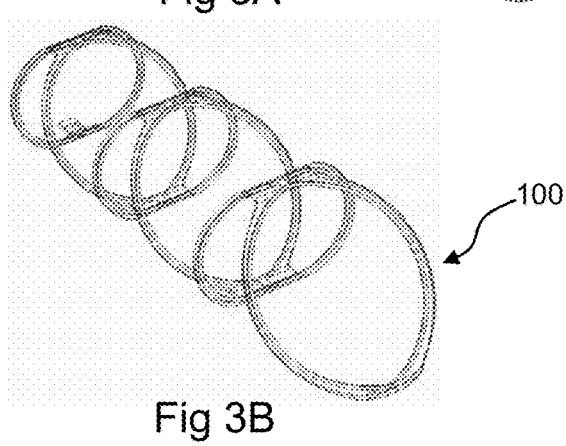
Figure 3C:
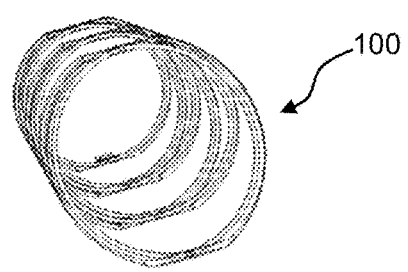
Figure 3D:
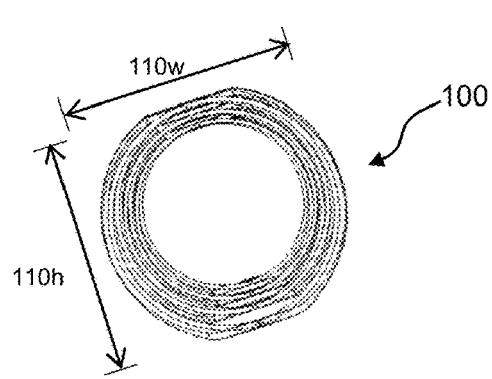

To provide further insight, FIGS. 3A-3D are wireframe illustrations of the occlusion device 100 of FIG. 1A, viewed from different perspectives. In FIG. 3D, the occlusion device 100 of FIG. 1A is viewed along its longitudinal axis. As can be seen from this figure, the loops 112 each has an outer edge that forms substantially circular shape when viewed along the longitudinal axes of the device. Upon implantation in a body lumen such as a blood vessel, this allows an outer edge of at least one loop 112 (in this case all loops 112) to contact a surrounding vessel wall along all or substantially all of a 360 degree rotation of the vessel wall (e.g., greater than or equal to 300 degrees of contact), thereby substantially completely blocking the vessel (so long as a covering material covers the orifice 112o of at least one loop). As previous noted, width 110w of FIG. 1A is the same as height 110h of FIG. 2B. As seen from FIG. 2D, these dimensions correspond to an effective diameter of the device.

It should be noted that increasing the number of loops will increase the resistance of the device 100 to migration within a body lumen. In this regard, more loops may be advantageous when prevention of both antegrade and retrograde flow is desired, such as in the treatment of bleeds or aneurysms of the viscera, among other applications. Because increasing the number of loops increases anchoring forcer in certain embodiments, if more anchoring force is desired, some of the redundant loops need not be covered but may serve the purpose to anchor the portions that are covered and executing the occlusive properties. More loops, however, also increase the length of the device as deployed, which may or may not be of importance, depending on the implant location.

It is further noted that a health practitioner may trim one or more loops from a multi-loop device in order to tailor the length of the device to the implant location.

Figure 7A:
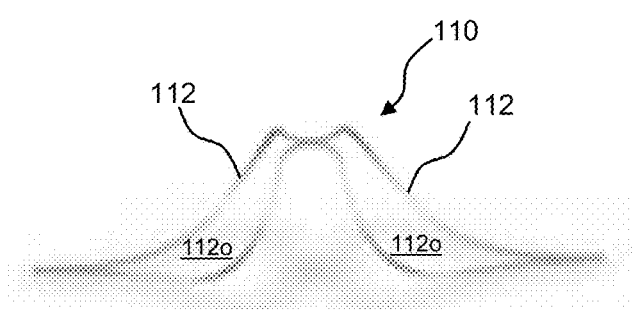
FIGS. 7A and 7B are schematic illustrations, taken from two different perspectives, of a support frame for use with an occlusion device in accordance with an embodiment of the present disclosure.
Figure 7B:
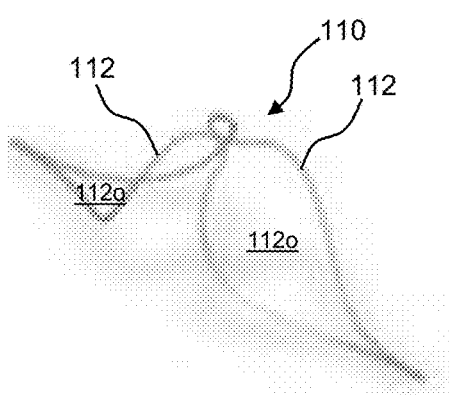

While the loops of the support frame of the occlusion device of FIGS. 2A-2D are substantially elliptical, as will be appreciated, other loop shapes are also possible, as long as the loop 112 has an outer edge that forms substantially circular shape when viewed along the longitudinal axes of the support frame 110. These include, but are not limited to teardrop shapes. In this regard, FIGS. 7A and 7B are schematic perspective views of a support frame 110 of an occlusion device which comprises two loops 112 that are generally teardrop in shape. As with of the support frame of FIGS. 2A-2D, the loops 112 are shaped such that, upon expansion in a tubular body lumen such as a blood vessel, edges of at least one loop 112 (in this case two loops) contacts a surrounding vessel wall along all or nearly all of a 360 degree rotation of the vessel wall, thereby substantially completely blocking the vessel so long as a covering material covers the orifice 112o of at least one loop.

The covering material 120 for the occlusion device 100 of FIG. 1A is shown in FIG. 1C. The covering material 120 may assist the device in slowing or immediately halting flow through a body lumen (e.g., blood flow), upon expansion of the support frame 110 in a body lumen (e.g., in a blood vessel). In the embodiment shown, the covering material covers the entirety of the support frame 110 except for the attachment feature 116 which is integral with the support frame 110. In other embodiments, however, the covering material 120 may only cover the orifice 112o of one or more of the loops 112. As will be appreciated from the axial wireframe perspective of FIG. 3D, a single covered orifice is sufficient to substantially block a circular cross-section of a body lumen such as a blood vessel. Thus, the covering material 120 may cover one, two, three, four, five or all six of the orifices 112o of the support frame 110, for example, in sequential arrangement or in alternating arrangement (e.g., where three alternating orifices 112o are covered).

In some embodiments, the covering 120 may be permeable to blood and/or other fluids, such as water. In some embodiments, the covering 120 may be impermeable such fluids. In some embodiments, a covering 120 may be selected that promotes endothelialization after implantation. Various materials suitable for use as covering materials in the present disclosure are discussed below.

In various embodiments, the occlusion device 100 may have unconstrained diameter that is, for example, 10% to 40% greater, among other values, than the diameter of a vessel to be embolized such that radial force assists in anchoring the device 100. Anchoring may also be assisted (or thwarted) by pressure associated with the direction of blood flow in various embodiments.

It is Further noted that by leaving a portion of the support frame 110 exposed, the device may be better able to engage surrounding tissue. For this reason, in various embodiments, one or more loops 112 of the support frame 110 are not provided with a covering material 120, in which case the uncovered loops may act as anchoring loops that resist migration after implantation in a body lumen. In various embodiments, outer tissue-engaging surfaces of at least some of the loops 112 may be roughened to better engage surrounding tissue, for example, where there is concern that the radial force exerted by the device will not be adequate to sufficiently anchor the device. This is particularly true of embodiments where blood is flowing in a distal-to-proximal direction and/or where the device is implanted in a vein (veins have a much higher compliance than arteries, largely due to their thinner walls), either or both of which may lead to an increase in likelihood that the device 100 may migrate. Alternatively or in addition, in certain embodiments the occlusion device may include a plurality of anchors (e.g., barbs, hooks, etc.) extending radially outward from the support frame such that they can engage tissue and inhibit longitudinal movement of the deployed occlusion device. For instance, a plurality of hooks or barbs may be provided on tissue contacting surfaces of one or more of the loops 112 of the support frame 110 or a plurality of hooks or barbs may be provided on tissue contacting surfaces of one or more of the connection regions 114 of the support frame 110.

In various embodiments, the occlusion devices described herein may be delivered via a tubular device (e.g., a catheter or a sheath inserted through a catheter) having a diameter ranging, for example, from 3 to 55%, more typically, from 4 to 21% of the unconstrained (fully expanded) diameter of the occlusion devices, among other values.

In various embodiments, a vessel occlusion device having a compressed diameter sufficiently small to occupy a 0.021 inch inner diameter catheter (i.e., less than 0.021 inch or 0.53 mm) may have an unconstrained diameter ranging, for example, from 2 mm to 6 mm, among other values. Such devices are, for instance, suitable for implantation in of a vessel having an inner diameter ranging, for example, from 1 mm to 4 mm, among other values. Such devices may have a deployed length less than, for example 12 mm, among other values.

A vessel occlusion device having a compressed diameter sufficiently small to occupy a 0.027 inch inner diameter catheter (i.e., less than 0.027 inch or 0.69 mm) may have an unconstrained diameter ranging, for example, from 3 to 7 mm, among other values. Such devices are, for example, suitable for implantation in a vessel having an inner diameter ranging, for example, from 2 mm to 5 mm, among other values. Such devices may have a deployed length that is, for example, less than 12 mm, among other values.

A vessel occlusion device having a compressed diameter sufficiently small to occupy a 5 French guide sheath having an inner diameter of approximately 0.067" (i.e., 1.67 mm) or a 6 French guiding catheter having an inner diameter of approximately 0.070" (1.8 mm) may have an unconstrained diameter ranging, for example, from 3 to 21 mm, more typically 12 to 21 mm, among other values. Such devices are, for example, suitable for embolization of a vessel having an inner diameter ranging, for example, from 2 mm to 18 mm, more typically, 5 mm to 14 mm, among other values, and may have a deployed length that less than 16 mm, among other values.

With regard to deployed length, it is noted that this length can be designed to be longer or shorter and is not dictated by catheter inner diameter, with lower loop angles will producing a longer occluder length, and vice versa. Deployment length is thus general design variable that can be adjusted as needed.

In some embodiments, the support frame may be formed of or comprise a metallic material, a metallic alloy, a ceramic material, a polymer, a metallic-polymer composite, a ceramic-polymer composite, combinations thereof, and the like. The material selected is preferably biocompatible and has a shape memory such that it is able to be compressed into a tube and self-expands upon being removed from the tube. Some specific examples of suitable materials may include metallic materials and/or alloys such as nickel-titanium alloy (nitinol) (e.g., super elastic or linear elastic nitinol), stainless steel (e.g., 303, 304v, or 316L stainless steel), nickel-chromium alloy, nickel-chromium-iron alloy, cobalt alloy, nickel, titanium, platinum, and the like. In various embodiments, the attachment feature may be formed from such materials as well.

Figure 5:
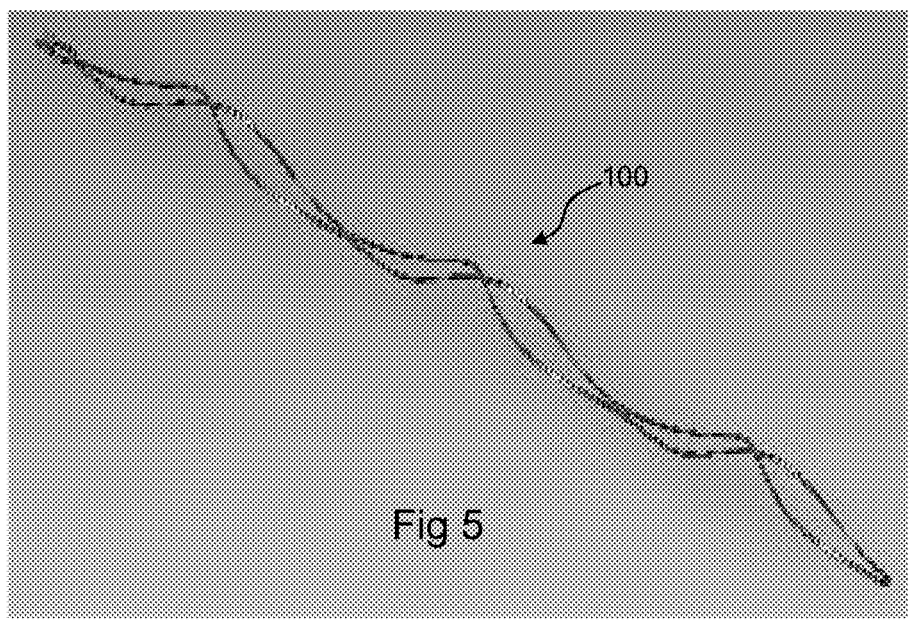
FIG. 5 is a schematic perspective view of a support frame of the occlusion device of FIG. 1A, as laser cut from a tube, in accordance with an embodiment of the present disclosure.

Support frames may be formed from these and other materials by various methods. For example, in certain embodiments, a support frame may cut from a tubular member, such as a metallic hypotube, or other suitable starting substrate. In some embodiments, the support frame may be laser cut from a single tubular member. The skilled artisan will recognize that various manufacturing methods known in the art may be used including, but not limited to, machining, chemical etching, water cutting, EDM, an so forth. In certain embodiments, the support frame may be formed in a mold from a melted material.

Where cut from a metallic tube, the support frame 110 may be initially cut from the metallic tube in a low profile configuration such as that shown in FIG. 5. Once formed in this manner, the support frame 110 may be placed in an expanded configuration, for example, by inserting a mandrel into center of the support frame 110 that has a diameter corresponding to the desired inner diameter of the device. To form a shape memory for the new configuration, the support frame 110 may be heat-treated for a suitable temperature and time, which will depend on the type of material being treated. For nitinol, the temperature may range from 460° C. to 530° C., more typically, 480° C. to 510° C., among other possibilities, and the time may vary from 1 to 30 minutes, more typically, 4 to 8 minutes, among other possibilities.

As previously noted, in some embodiments, an attachment feature 116 may be integrally formed with the support frame 110. In some embodiments, an attachment feature 116 may be attached to the support frame 110 after support frame formation.

In various embodiments, the occlusion device 100 may include imaging markers, for example, radiopaque markers, which may be positioned at various points along the device 100, so as to provide information on the position and/or orientation of the device 100. For example, radiopaque markers may be provided at points associated with the loops 112, the connection regions 114, or both. Radiopaque markers may be for example, attached, electroplated, dipped and/or coated at one or more locations along the support frame 110. Radiopaque materials are understood to be materials capable of producing a relatively bright image on a fluoroscopy screen or another imaging technique such as X-ray during a medical procedure. This relatively bright image aids the user of the device in determining its location. Suitable radiopaque materials may include, but are not limited to metals such as gold, platinum, palladium, tantalum, tungsten, metal alloys comprising one or more of the preceding metals, bismuth subcarbonate, iodine and the like. In certain beneficial embodiments, radiopaque materials may be positioned at the connection regions 114 between the loops 112, among other possibilities.

In some embodiments, the covering materials may be formed of or include a polymeric material, a metallic or metallic alloy material, a metallic-polymer composite, combinations thereof, and the like. In some embodiments, the covering is beneficially formed of biostable or biodegradable materials, depending on whether it is desired to create a temporary or permanent occlusion. Typical thicknesses for the covering materials range, for example, from 0.00015" (0.0038 mm) to 0.004" (0.1 mm), among other values. In some embodiments, the covering material may be porous.

Permanent covering materials may be constructed of very fine microfibers. The microfibers may be knitted, braided, woven, or electrostatically spun into a very thin yet strong membrane. Beneficial materials for the fibers include polyesters such as polyethylene terephthalate (PET), fluoropolymers such as polytetrafluoroethylene (PTFE) and polyvinylidene difluoride (PVDF), polyalkylenes such as polyethylene, polyamides such as nylon, polyurethane, or other suitable biostable materials known in the art. Thin membranes of expanded polytetrafluoroethylene (ePTFE) are also beneficial. Temporary covering materials may be formed from polyesters such as polylactide, polyglycolide, poly(lactide-co-glycolide), or other suitable biodegradable materials known in the art, using many of the same processes. Temporary covering materials may also be formed from natural tissue such as human tissue and decellularized plant and animal tissue. Human tissues may be derived, for example, from human cadaveric or engineered human tissue. Animal tissues may be derived, for example, from porcine, ovine, bovine, and equine tissue sources, among many others. One specific example is a urinary bladder matrix (UBM) film comprising extracellular matrix derived from porcine urinary bladder, such as that available from ACell Inc., Columbia, Md., USA.

As described herein, a number of methods exist for attaching the covering material 120 to the support frame 110. For example, covering material 120 may be secured to the support frame 110 through the use of biocompatible staples, sutures or combinations thereof. In some embodiments, the support frame 110 may include a plurality of barbs or other anchors, which may project through the covering material 120, holding it in place. The covering material 120 may be secured to the support frame 110 by heat sealing, solvent bonding, adhesive bonding, or welding the covering material 120 to itself and/or to the support frame 110. Various techniques may be also be employed to laminate or bond a first sheet of covering material 120 to an second sheet of covering material 120, such that portions of the frame are encapsulated between the sheets (e.g., at least one loop 112, thereby covering the orifice 112a formed by the loop 112). Heat sealing, solvent bonding, adhesive bonding, application of force or other bonding techniques may all be employed to bond or secure the sheets of covering material 120 to one another.

Regardless of whether a temporary or permanent covering material 120 is employed. Due to the circular profile of the various occlusion devices 100 described herein when viewed from a longitudinal axial perspective, a healthcare practitioner may, subsequent to implantation, perforate the covering material, optionally with stenting, to restore flow. Other types of occlusion devices may be less symmetric, such as a coils, and may not lend themselves to being reopened or accessed via direct perforation followed by establishment of routine lumen flow using techniques such as stenting.

In some embodiments, the occlusion device may be coated with, or may otherwise include a material that provides a smooth, slick outer surface. In some embodiments, the occlusion device may include or be coated with a lubricious coating, a hydrophilic coating, a hydrophobic coating, a drug-containing coating, or other suitable coating depending on the intended use or application. In some embodiments, occlusion device may include a thrombotic agent and/or an endothelialization-promoting agent.

In some embodiments, occlusion devices are provided in conjunction with a delivery system that includes an elongate delivery member and tubular delivery device.

Figure 6A:
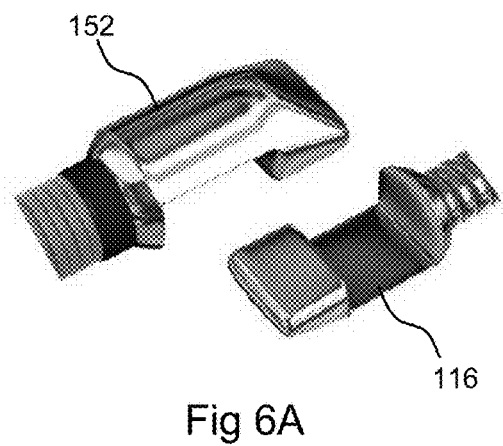
FIG. 6A is a schematic perspective view of an attachment mechanism of a delivery catheter and a complementary attachment feature of an occlusion device, in accordance with an embodiment of the present disclosure.
Figure 6B:
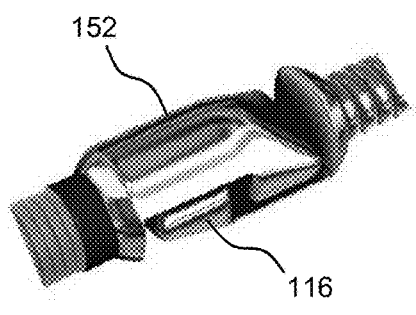
FIG. 6B is a schematic perspective view of the elements of FIG. 6A in a stacked engaged relationship.

With reference to FIGS. 4A-4C, for delivery, the occlusion device 100 may be compressed within a lumen of a tubular device such as a delivery catheter 160, in a constrained position. (As previously indicated, while the occlusion device 100 shown comprises two loops 100, one covered and one uncovered, the present disclosure is not so limited.) An elongate delivery member such as a delivery shaft 150 may also be disposed within the lumen of the delivery catheter 160 and may be reversibly connected to the occlusion device 100 at the proximal attachment feature 116, such that the occlusion device 100 can be advanced and withdrawn relative to the catheter 160 as desired and eventually released within the body. In some embodiments, the delivery shaft 150 may comprise an attachment mechanism that is configured to engage an attachment feature of the implantable device. For example, the delivery shaft 150 may comprise an attachment mechanism that is configured to engage a slot like that shown in the attachment feature 116 shown in FIGS. 1A-3D. As another example, the delivery shaft 150 may comprise an attachment mechanism 152 like that shown in FIG. 6A while the occlusion device 100 may comprise an attachment feature 116 that is complementary in shape to the attachment mechanism 152. While in the delivery catheter 160, these elements 152,116 are constrained in a clasped configuration like that shown in FIG. 6B, preventing them from disengaging. Once elements are 152,116 emerge from a distal end of the catheter, they may be readily separated, for example, by rotating the delivery shaft 150. As yet another example, the delivery shaft 150 may comprise a threaded male fitting at its distal end which is threaded into a female threaded fitting within the attachment feature of the occlusion device 100, or vice versa, among various other possible mechanical or electrical (e.g., electrolytic dissolution, etc.) means of forming such a reversible connection. The delivery catheter 160, occlusion device 100 and delivery shaft 150 collectively form a delivery system.

During delivery, the delivery system may be percutaneously inserted into a patient to deliver the occlusion device 100 to a desired vascular site 200 (e.g., an artery, vein, etc.). Access to an artery or vein to be embolized may be achieved via the femoral artery, femoral vein, or radial artery, among other access points. Initially, the occlusion device 100 (plan view shown) may be disposed in a first, constrained position within the lumen of the delivery catheter 160, as shown in FIG. 4A.

Upon reaching the desired delivery location, the delivery catheter 160 may be withdrawn proximally while keeping the delivery shaft stationary, or the delivery shaft 150 may be advanced distally while the delivery catheter 160 is held stationary (i.e., relative movement between the delivery catheter and the delivery shaft 150 is created), such that the occlusion device 100 emerges from the delivery catheter 160 and self-expands radially outward to an expanded position where the support frame may extend radially outward such that the outer surface of the occlusion device 100 conforms to the wall of the vessel 200 as shown in FIG. 4B. Depending on the nature of the linkage between the delivery shaft 150 and the occlusion device 100, the occlusion device 100 may be recaptured by pulling the occlusion device 100 back into the delivery catheter 160, in some embodiments.

Lastly, delivery shaft 150 may be disconnected from the occlusion device 100 (if not previously released) and the delivery catheter 160 and delivery shaft 150 removed from the patient, leaving the occlusion device at the vascular site 200 as shown in FIG. 4C. Once implanted, the covering material acts to slow or halt the blood flow, and the entire device may act as a substrate for coagulation, creating a permanent embolus if desired. In certain beneficial embodiments, the occlusion device 100 becomes integrated to the vascular tissue.

Using these and other procedures, the occlusion devices described herein may be implanted in a variety of body lumens including spermatic ducts, fallopian tubes, and blood vessels. Where used for embolization, the devices described herein may be implanted into a wide variety of blood vessels, including a wide variety of arterial and venous blood vessels. Examples of arteries in which the devices may be implanted include following arteries (including any divisions thereof): the internal iliac artery (hypogastric artery), external iliac artery, gastroduodenal artery, renal artery, hepatic artery, uterine artery, lienal artery, splenic artery, intercostals artery, mesenteric artery, right gastric artery, left gastric artery, lumbar artery, internal carotid artery, communicating artery, basilar artery, bronchial artery, cerebral artery, cerebellar artery, profunda femoris artery, gastroepiploic artery, and pancreaticoduodenal artery, among others. Examples of veins in which the blood vessel embolization devices may be implanted include a pelvic vein, internal iliac vein (hypogastric vein), portal vein and gonadal veins (e.g. spermatic vein or ovarian vein, depending on gender), among others. Examples of blood vessels in which the blood vessel embolization devices may be implanted further include abnormal blood vessels, for example, arteriovenous fistulas and arteriovenous malformations, among others.

In particularly beneficial embodiments, occlusion devices as described herein may be employed to perform prophylactic gastroduodenal artery embolization (the gastroduodenal artery is a branch of the common hepatic artery) and/or right gastric artery embolization, for example, prior to Y90 therapy or other microsphere therapy for hepatocellular carcinoma or liver metastases (e.g. drug eluting microspheres, TACE, etc.) as well as to perform prophylactic hypogastric embolization (the hypogastric artery is also known as the internal iliac artery) prior to AAA stent graft implantation. Each of these procedures requires embolization of the ostium of an artery.

The blood vessel occlusion devices described herein are advantageous in these and other procedures in that they are configured to block a body lumen (e.g., blood vessel) with only a single deployment, while at the same time resisting kickback into a parent artery (e.g., when placed at a blood vessel ostium), due to the fact that they have a highly defined shape upon deployment (and due to the direction of blood flow in some embodiments).

In another aspect of the disclosure, medical kits useful in embolization procedures are provided. The medical kits may include all or a subset of all the components useful for performing the procedures. For example, the medical kits may comprise any combination of any two, three, four, or more of the following items: (a) an occlusion device as described herein, (b) a tubular device (e.g., a catheter and/or sheath) suitable for delivering the vessel occlusion device (in certain beneficial embodiments, the vessel occlusion device may be compressed and preloaded into the tubular device in a constrained, i.e., reduced diameter, shape), (c) an elongate delivery member such as a delivery shaft, which may be reversibly connected to the occlusion device via a suitable mechanism such as one of those described herein, (d) a catheter introducer, (f) suitable packaging material, and (g) printed material with one or more of the following: storage information and instructions regarding how to deploy the occlusion device in a subject.

Although various embodiments are specifically illustrated and described herein, it will be appreciated that modifications and variations of the present disclosure are covered by the above teachings and are within the purview of the appended claims without departing from the spirit and intended scope of the disclosure.

What is claimed is:

1. An occlusion device comprising:
   (a) a self-expanding support frame having a longitudinal axis comprising a plurality of loops, each loop having an end connected to at least one other adjacent loop by a joint, each joint being in a respective plane parallel to the longitudinal axis, each joint having a width dimension in the respective plane along the longitudinal axis greater than a thickness dimension in the respective plane along an axis perpendicular to the longitudinal axis, each loop having an orifice, said support frame being self-expandable from a constrained shape to an unconstrained shape; and
   (b) a material covering the orifice of at least one of the loops and at least one joint;
   wherein the plurality of loops comprises three to eight loops; and
   wherein the joints along the support frame between adjacent loops alternate between being in the same respective plane above the longitudinal axis and being in the same respective plane below the longitudinal axis.

2. The occlusion device of claim 1, wherein at least one loop is uncovered.

3. The occlusion device of claim 1, wherein when the support frame is viewed axially the loops have a substantially circular shape.

4. The occlusion device of claim 1, wherein the plurality of loops of the support frame comprises a series of elliptical loops.

5. The occlusion device of claim 1, wherein each loop ranges from 60° to 170° out of coplanar with an adjacent loop when in the unconstrained shape.

6. The occlusion device of claim 1, wherein an elevation view of the support frame comprises a cosinusoidal shape.

7. The occlusion device of claim 6, wherein the cosinusoidal shape comprises inflection points at the joints having tangents that range from 30° to 85° relative to the longitudinal axis when in the unconstrained shape.

8. The occlusion device of claim 1, further comprising an attachment feature.

9. The occlusion device of claim 1, further comprising a plurality of anchors.

10. The occlusion device of claim 1, wherein the material comprises a porous woven or non-woven polymeric sheet.

11. The occlusion device of claim 1, wherein the occlusion device is compressed and preloaded into a tubular device in said constrained shape.

12. A method of treatment comprising:
   (a) introducing the occlusion device of claim 1 into a blood vessel while in said constrained shape; and
   (b) removing a constraint that maintains the occlusion device in said constrained shape such that the support frame self-expands, the loops contact a wall of the blood vessel, and the material impedes flow through the blood vessel.

13. The method of claim 12, wherein the constraint is removed by ejecting the occlusion device from a tubular medical device.

14. The method of claim 12, wherein the blood vessel is selected from a gastroduodenal artery, a hypogastric artery, and right gastric artery.

15. A kit comprising:
   (a) an occlusion device comprising: (i) a self-expanding support frame having a longitudinal axis comprising a plurality of loops, each loop having an end connected to at least one other adjacent loop by a joint, each joint being in a respective plane parallel to the longitudinal axis, each joint having a width dimension in the respective plane along the longitudinal axis greater than a thickness dimension in the respective plane along an axis perpendicular to the longitudinal axis, each loop having an orifice, said support frame being self-expandable from a constrained shape to an unconstrained shape and (ii) a material covering the orifice of at least one of the loops and at least one joint; and
   (b) at least one article selected from (i) an elongate delivery member configured to be attached to and detached from the occlusion device, (ii) a catheter or sheath suitable for delivering the occlusion device to an occlusion site, or (iii) a catheter introducer;
   wherein the plurality of loops comprises three to eight loops; and
   wherein the joints along the support frame between adjacent loops alternate between being in the same respective plane above the longitudinal axis and being in the same respective plane below the longitudinal axis.

16. The kit of claim 15, wherein the elongate delivery member is a catheter.

17. An occlusion device comprising:
   (a) a self-expanding support frame having a longitudinal axis comprising a plurality of loops, each loop having an end connected to at least one other adjacent loop by a joint, each joint being in a respective plane parallel to the longitudinal axis, each joint having a width dimension in the respective plane along the longitudinal axis greater than a thickness dimension in the respective plane along an axis perpendicular to the longitudinal axis, each loop having an orifice, said support frame being self-expandable from a constrained shape to an unconstrained shape; and
   (b) a material covering the orifice of at least one of the loops and at least one joint;
   wherein an elevation view of the support frame comprises a cosinusoidal shape.

18. The occlusion device of claim 17, wherein at least one loop is uncovered.

19. The occlusion device of claim 17, wherein when the support frame is viewed axially the loops have a substantially circular shape.

20. The occlusion device of claim 17, wherein the plurality of loops of the support frame comprises a series of elliptical loops.

* * * * *